United States Patent
Huizenga et al.

(10) Patent No.: US 10,246,390 B2
(45) Date of Patent: Apr. 2, 2019

(54) PROCESS FOR THE SEPARATION OF GLYCOLS USING GLYCEROL

(71) Applicant: SHELL OIL COMPANY, Houston, TX (US)

(72) Inventors: Pieter Huizenga, Amsterdam (NL); Kai Jurgen Fischer, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 42 days.

(21) Appl. No.: 15/533,815

(22) PCT Filed: Dec. 4, 2015

(86) PCT No.: PCT/EP2015/078680
§ 371 (c)(1),
(2) Date: Jun. 7, 2017

(87) PCT Pub. No.: WO2016/091751
PCT Pub. Date: Jun. 16, 2016

(65) Prior Publication Data
US 2017/0334816 A1  Nov. 23, 2017

(30) Foreign Application Priority Data
Dec. 8, 2014 (EP) ..................... 14196838

(51) Int. Cl.
*C07C 29/84* (2006.01)
*B01D 3/40* (2006.01)
(Continued)

(52) U.S. Cl.
CPC ............... *C07C 29/84* (2013.01); *B01D 3/40* (2013.01); *B01D 3/4294* (2013.01); *C07C 29/80* (2013.01); *C07C 31/202* (2013.01); *C07C 31/207* (2013.01)

(58) Field of Classification Search
CPC ....... C07C 29/84; C07C 31/202; C07C 29/80; C07C 31/207; B01D 3/40; B01D 3/4294
See application file for complete search history.

(56) References Cited

U.S. PATENT DOCUMENTS 4,935,102 A * 6/1990 Berg ....................... C07C 29/82
203/58
4,966,658 A   10/1990 Berg
(Continued)

FOREIGN PATENT DOCUMENTS

| CN | 102643165 B | 7/2014 |
| EP | 3126315 A1 | 2/2017 |
| WO | 2014193889 A1 | 12/2014 |

OTHER PUBLICATIONS

International Search Report and Written Opinion received for PCT Patent Application No. PCT/EP2015/078680, dated Jan. 25, 2016, 9 pages.
(Continued)

*Primary Examiner* — Renee Robinson
*Assistant Examiner* — Derek N Mueller

(57) ABSTRACT

A process for the separation of monoethylene glycol (MEG) and 1,2-butanediol (1,2-BDO) from a first mixture including MEG and 1,2-BDO, the process including providing the first mixture of MEG and 1,2-BDO as a feed to a distillation column. The process also includes providing a feed comprising glycerol to the distillation column above the first mixture. The process also includes operating the distillation column at a temperature in the range of from 50 to 250° C. and a pressure in the range of from 0.1 to 400 kPa. The process also includes removing a stream comprising MEG and glycerol as a bottoms stream from the distillation column and removing a stream comprising 1,2-BDO above the point at which the feed comprising glycerol is provided to the distillation column.

9 Claims, 1 Drawing Sheet

(51) Int. Cl.
*C07C 29/80* (2006.01)
*B01D 3/42* (2006.01)
*C07C 31/20* (2006.01)

(56) References Cited

U.S. PATENT DOCUMENTS

| | | |
|---|---|---|
| 5,423,955 A | 6/1995 | Berg |
| 2011/0312050 A1 | 12/2011 | Zhang et al. |
| 2013/0284584 A1 | 10/2013 | Xiao et al. |

OTHER PUBLICATIONS

Rogalski et al., "Ebulliometers modified for the accurate determination of vapour-liquid equilibrium", Fluid Phase Equilibria, vol. 5, Issues 1-2, 1980, pp. 97-112.

\* cited by examiner

VLE data for MEG/1,2-BDO molar ratio of 0.58/0.42 at 20.7 mbar with Glycerol: relative volatility of MEG vs. 1,2-BDO

PROCESS FOR THE SEPARATION OF GLYCOLS USING GLYCEROL

PRIORITY CLAIM

The present application is the National Stage (§ 371) of International Application No. PCT/EP2015/078680, filed Dec. 4, 2015, which claims priority from European Patent Application No. 14196838.8, filed Dec. 8, 2014 incorporated herein by reference.

FIELD OF THE INVENTION

The present invention relates to a process for the selective separation of glycols.

BACKGROUND OF THE INVENTION

Ethylene glycol and propylene glycol are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as sugar-based materials. For example, US 2011/312050 describes a continuous process for the catalytic generation of polyols from cellulose, in which the cellulose is contacted with hydrogen, water and a catalyst to generate an effluent stream comprising at least one polyol.

CN 102643165 is directed to a catalytic process for reacting sugar in an aqueous solution with hydrogen in the presence of a catalyst in order to generate polyols.

As with many chemical processes, the reaction product stream in these reactions comprises a number of desired materials, diluents, by-products and other undesirable materials. In order to provide a high value process, the desirable product or products must be obtainable from the reaction product stream in high purity with a high percentage recovery of each product and with as low as possible use of energy and complex equipment.

In known processes to make glycols, the glycols are usually present at high dilution in a solvent, typically water. The water is usually removed from the glycols by distillation. Subsequent purification of the glycols is then carried out by fractional distillation. This process can have high costs both in terms of capital and operational expenditure. Further, repeated heating or maintenance at raised temperatures in the distillation steps may also lead to decomposition of the desired glycol products.

When glycols are produced by hydrogenolysis of sugars, a mixture of glycols is produced. The main glycol constituents in the reaction product stream are monoethylene glycol (MEG), monopropylene glycol (MPG) and 1,2-butanediol (1,2-BDO). The separation of these glycols by fractional distillation is complicated due to the similarity in boiling points, particularly between MEG and 1,2-BDO (respectively 198 and 196.8° C.). Further, the isolation of a pure MEG overheads stream by fractional distillation from a mixture comprising MEG and 1,2-BDO is made impossible by the formation of a homogeneous minimum boiling azeotrope between MEG and 1,2-BDO at atmospheric pressure. Degradation of the products at high temperatures prevents higher than atmospheric pressure being used for distillation.

U.S. Pat. No. 4,966,658 is directed to the separation of a mixture of 1,2-BDO and MEG using a process known as azeotropic distillation in which an azeotrope-forming agent is added to the mixture before distillation in order to facilitate separation. A similar process is described in U.S. Pat. No. 5,423,955 for the separation of 1,2-BDO and MPG. Azeotropic distillation can lead to an increase in relative volatility between the components but also leads to further process steps in order to remove the azeotrope forming agents.

Another azeotropic distillation method is described in US20130284584. This document describes the use of an azeotropic agent of structural formula:

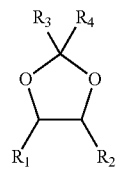

wherein each R group is hydrogen or an alkyl group.

Co-pending application EP 14163242.2 discloses a process for separating monoethylene glycol from a mixture comprising monoethylene glycol and 1,2-butanediol, using a two column, pressure-swing distillation set-up.

It would be advantageous to provide a simple and efficient method suitable for the recovery of MEG from a mixture comprising MEG and 1,2-BDO.

SUMMARY OF THE INVENTION

Accordingly, the present invention provides a process for the separation of MEG and 1,2-BDO from a first mixture comprising MEG and 1,2-BDO, said process comprising the steps of:
(i) providing said first mixture comprising MEG and 1,2-BDO as a feed to a distillation column;
(ii) providing a feed comprising glycerol to the distillation column above the first mixture;
(iii) operating the distillation column at a temperature in the range of from 50 to 250° C. and a pressure in the range of from 0.1 to 400 kPa;
(iv) removing a stream comprising MEG and glycerol as a bottoms stream from the distillation column; and
(v) removing a stream comprising 1,2-BDO above the point at which the feed comprising glycerol is provided to the distillation column.

DETAILED DESCRIPTION OF THE INVENTION

Figure 1:
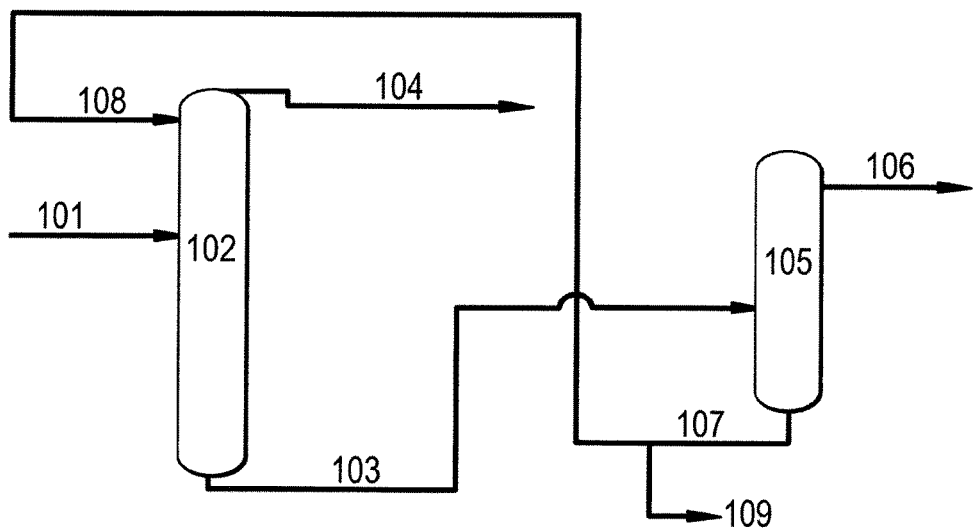
FIG. 1 is a schematic diagram of an exemplary, but non-limiting, embodiment of a process for the separation of glycols as described herein.

The present inventors have found that MEG can be effectively separated with high recovery and excellent MEG product purity from a mixture comprising MEG and 1,2-BDO by distilling said mixture in a distillation column wherein a feed of glycerol is provided to the top of the column. The presence of glycerol in the distillation column changes the relative volatilities of MEG and 1,2-BDO and breaks the azeotrope that exists between the two.

The term glycol as used herein is given its usual meaning, i.e. a diol in which the two hydroxyl groups are present on vicinal carbon atoms.

The process may be applied to any mixture comprising MEG and 1,2-BDO. Preferably, the first mixture comprising MEG and 1,2-BDO is derived from the reaction product stream from a process for the production of glycols. In a particularly preferred embodiment of the invention, the first mixture comprising MEG and 1,2-BDO is derived from the reaction product stream from a process for the hydrogenolysis of a saccharide-containing feedstock.

Typically, the reaction product stream from a process for the hydrogenolysis of a saccharide-containing feedstock comprises, as glycols, at least MEG, MPG and 1,2-BDO. These glycols are typically present at a concentration in the range of from 0.1 to 30 wt % of the overall stream.

In such a reaction product stream, MEG is suitably present as at least 10 wt %, preferably as at least 30 wt % of the non-solvent fraction of the stream. MEG is suitably present as at most 95 wt %, preferably as at most 90 wt %, most preferably as at most 80 wt % of the non-solvent fraction of the stream.

In such a reaction product stream, MPG is suitably present as at least 2 wt %, preferably as at least 4 wt % of the non-solvent fraction of the stream. MPG is suitably present as at most 45 wt %, preferably as at most 20 wt % of the non-solvent fraction of the stream.

In such a reaction product stream, 1,2-BDO is suitably present as at least 1 wt %, preferably as at least 4 wt % of the non-solvent fraction of the stream. 1,2-BDO is suitably present as at most 20 wt %, preferably as at most 8 wt % of the non-solvent fraction of the stream.

As well as the glycols, the reaction product streams from hydrogenolysis reactions of saccharides may comprise solvent (particularly water), oxygenates, hydrocarbons, catalyst, degradation products, and gases in any composition. The variety of compounds and their concentration depend on the saccharide-containing feedstock and the various hydrogenation and hydrogenolysis conversion conditions, including catalysts, reaction conditions such as temperature, pressure and saccharide concentration. However, suitably the hydrogenolysis reactions have gone to completion and the aqueous stream contains less than 5 wt %, preferably less than 2 wt %, more preferably less than 1 wt %, even more preferably less than 0.5 wt %, most preferably substantially no saccharides when considered as a weight percentage of the overall stream. Typically, the aqueous stream also contains less than 5 wt %, preferably less than 2 wt %, more preferably less than 1 wt %, even more preferably less than 0.5 wt %, most preferably substantially no glycerol, when considered as a weight percentage of the overall stream.

If the first mixture comprising MEG and 1,2-BDO is derived from such a reaction product stream, one or more treatment, separation and/or purification steps may be applied to the reaction product stream before the process of the present invention. Such steps may include one or more of: removal of at least a portion of the solvent present, for example by distillation; removal of light ends; fractional distillation to produce a glycols stream and removal of heavy organics and any inorganics present, such as catalyst material; and initial separation steps to achieve preliminary separation of glycols, e.g. separation of MPG by fractional distillation or other distillation process that results in a stream in which essentially all of the glycols remaining are MEG and 1,2-BDO, with trace amounts of higher glycols, such as 2,3-butanediol, 1,2-pentanediol and 1,2-hexanediol.

The mixture comprising MEG and 1,2-BDO preferably has a weight ratio of MEG:1,2-BDO of at least 5:1. More preferably the weight ratio of MEG:1,2-BDO is at least 25:1. Optionally, MPG is also present in the mixture comprising MEG and 1,2-BDO. In this embodiment of the invention, MPG typically comprises in the range of from 2 to 45 wt % of the mixture comprising MEG and 1,2-BDO.

The first mixture is provided as a feed to a distillation column. The column may be any suitable sort of column known in the art and may be equipped with trays or structured or unstructured packing. The number of theoretical trays may vary in the range of from 3 to 140 and may easily be determined by the skilled person on the basis of simple economic optimization experiments.

A feed comprising glycerol is provided to the distillation column above point at which the first mixture feed is provided. Preferably, the feed comprising glycerol is provided at the top of the column or a few trays below the top of the column. Most preferably, the feed comprising glycerol is provided at the top of the column. As well as glycerol, this stream may also comprise glycerol-like heavies, such as other polyhydric alcohols, from a recycle stream in the process.

Preferably, the glycerol is added in an amount such that the weight ratio of the feed comprising glycerol to the first mixture comprising MEG and 1,2-BDO is at least 1:20, more preferably at least 1:10, even more preferably at least 1:4, based on the overall weight of the feed/mixture. Preferably, the ratio of the feed comprising glycerol to the first mixture comprising MEG and 1,2-BDO is at most 10:1, more preferably at most 5:1, even more preferably 2:1, more preferably at most 1.5:1, based on the overall weight of the feed/mixture. The distillation is carried out at a temperature in the range of from 50 to 250° C., preferably of from 100 to 200° C. and at a pressure of at least 0.1 kPa, preferably at least 10 kPa, more preferably at least 50 kPa. The pressure is at most 400 kPa, preferably at most 200 kPa, more preferably at most 120 kPa. It will be clear to the skilled person to vary the temperature and pressure in relation to each other in order to achieve suitable conditions.

A stream comprising 1,2-BDO is removed from the distillation column above the point at which the feed comprising glycerol is provided to the distillation column. Preferably, the 1,2-BDO stream is removed from the distillation column as a condensed overheads stream. In the embodiment of the invention wherein MPG is also present in the mixture comprising MEG and 1,2-BDO, MPG will also be present in the overheads stream. MPG and 1,2-BDO may then be separated from each other in a separate fractional distillation step. Alternatively, the distillation column may be set up such that the two product streams are removed in the top of the distillation column, with the overheads stream comprising MPG and a side stream comprising the 1,2-BDO being removed at some point below the overheads stream and above the glycerol feed.

A stream comprising MEG and glycerol is removed from the distillation column as a bottoms stream. Suitably, the glycols content of this stream, comprises at least 95 wt % MEG, preferably at least 98 wt % MEG, more preferably at least 99 wt % MEG, even more preferably at least 99.5 wt % MEG, most preferably at least 99.6 wt % MEG. This stream may then be subjected to a further distillation step in which MEG is distilled off to provide an MEG stream and a glycerol stream. This distillation is carried out at lower pressure or higher temperature than in the extractive distillation step. At least a portion of the MEG content is recovered as a high purity MEG product.

The glycerol stream may then be recycled to the distillation column as the feed comprising glycerol. Any heavies left that had been present in the first mixture comprising MEG and 1,2-BDO will also be present in the glycerol stream to be recycled. If the first mixture comprising MEG and 1,2-BDO is derived from the reaction product stream from a process for the hydrogenolysis of a saccharide-containing feedstock, such heavies are likely to be glycerol like in their structure, boiling point and other physical properties and may be recycled with the rest of the glycerol stream.

A portion of this glycerol stream may be removed as a bleed in order to prevent a build-up of heavies. Optionally, at least a portion of the glycerol stream may be subjected to further processing steps to further increase its purity. Optionally, the MEG stream may be subjected to further processing steps to further increase its purity.

DETAILED DESCRIPTION OF THE DRAWINGS

The present invention is further illustrated in the preferred, but non-limiting, embodiment of the invention illustrated in FIG. 1.

In FIG. 1, a first mixture comprising MEG and 1,2-BDO is provided as a feed 101 to a distillation column 102. A feed 108 comprising glycerol is also provided to the top of the distillation column 102. The distillation is operated under conditions such that a stream 103 comprising MEG and glycerol is removed from the distillation column 102 as a bottoms stream and a stream 104 comprising 1,2-BDO is also removed from the distillation column 102 as an overheads stream. The stream 103 comprising MEG and glycerol is provided to a second distillation column 105, which is then operated to provide MEG as an overheads stream 106. The remaining glycerol is removed as the bottoms stream 107 of the second distillation column 105 and can be recycled to provide the feed 108 comprising glycerol. A bleed stream 109 is removed from the glycerol recycle stream in order to prevent a build-up of heavies.

EXAMPLES

The invention will be further illustrated by the following, non-limiting examples.

Example 1

Isobaric Vapour-Liquid Equilibrium (VLE) data were measured by means of a dynamic method using a Swietoslawski ebulliometer as described by Rogalski and Malanowski, Fluid Phase Equilib. 5 (1980) 97-112. At a given pressure, which is regulated by an electronic pressure control, the boiling temperature of a mixture can be measured. When phase equilibrium is reached, i.e. a stable circulation is achieved and the boiling temperature is constant, the concentrations of both phases in equilibrium can be determined by taking samples from the liquid and the condensed vapour phase and gas chromatographic analysis. Such data correspond to the separation on one theoretical plate in a distillation column.

For the ternary system MEG+1,2-BDO+glycerol isobaric VLE data were measured at 20.7 mbar with fixed glycerol feed concentrations (33.3 wt. % and 50 wt. %, respectively).

A glycerol-free data point was measured as reference at a boiling point of 98.77° C., with a MEG mole fraction of 0.5825 and a 1,2-BDO mole fraction of 0.4175 in the liquid phase (x(MEG) and x(1,2-BDO)), and a MEG mole fraction of 0.5745 and a 1,2-BDO mole fraction of 0.4255 in the vapour phase (y(MEG) and y(1,2-BDO)). These data can be converted into distribution coefficients (K-values), where K(MEG) is equal to the vapour phase mole fraction of MEG divided by the liquid phase mole fraction of MEG. Similarly, the K-value of 1,2-BDO is calculated using the mole fractions of 1,2-BDO in the vapour and liquid phases. The relative volatility alpha(MEG/1,2-BDO) can be defined as the ratio of the K-values of MEG and 1,2-BDO. At the azeotropic point, this relative volatility is 1 (one). The efficiency (selectivity and capacity) of a solvent to enhance the separation of MEG from 1,2-BDO can be assessed by monitoring the change of the relative volatility when different amounts of the solvent are added.

The following table summarizes the full set of VLE data as well as the derived K-values of MEG and 1,2-BDO and the relative volatility of MEG versus 1,2-BDO.

An alpha value lower than 1 means that the first component is heavy and will move down in the distillation column. The second component is lighter and will move up in the column.

The data show that MEG is the heavy component and 1,2-BDO is the light component. This effect is strengthened by adding glycerol as a solvent that preferably dissolves MEG and to a lesser extent 1,2-BDO.

Figure 2:
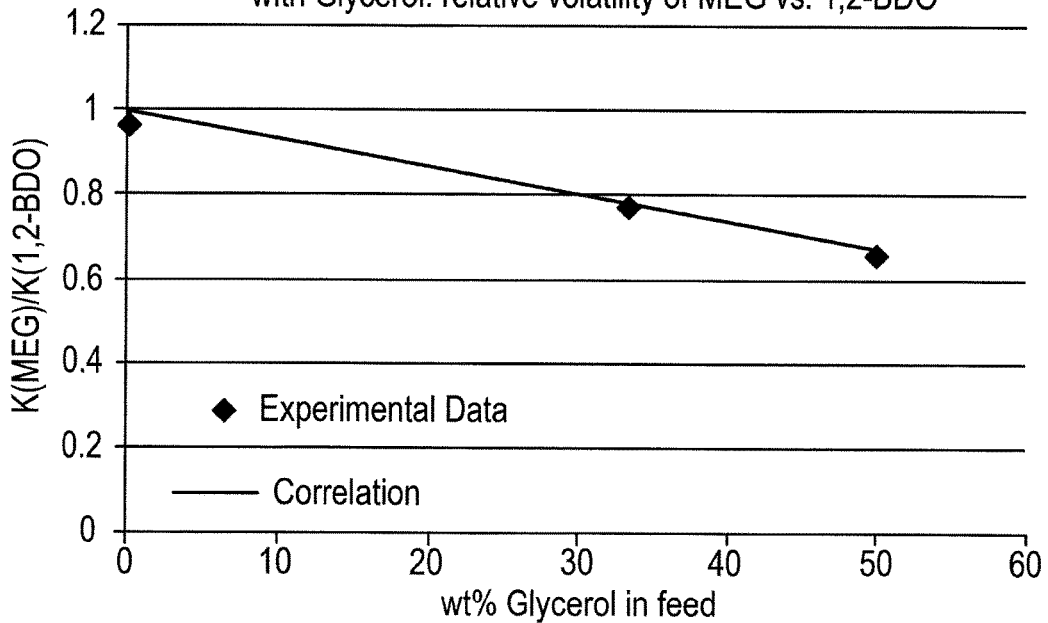
FIG. 2 shows VLE data for the Examples.

This effect is illustrated in FIG. 2, where the relative volatility (alpha(MEG/1,2-BDO)) is plotted against the glycerol content in the feed of the experiments and decreases with the amount of glycerol in the feed and subsequently in the liquid phase.

TABLE 1

| | liquid phase composition | | | vapor phase composition | | | | | alpha(MEG/ |
|---|---|---|---|---|---|---|---|---|---|
| T/° C. | x(MEG) | x(1,2-BDO) | x(glycerol) | y(MEG) | y(1,2-BDO) | y(glycerol) | K(MEG) | K(1,2-BDO) | 1,2-BDO) |
| | no glycerol in feed | | | | | | | | |
| 98.77 | 0.5825 | 0.4175 | 0.0000 | 0.5745 | 0.4255 | 0.0000 | 0.986 | 1.019 | 0.968 |
| | 33.3 wt. % glycerol in feed | | | | | | | | |
| 106.32 | 0.0000 | 0.6690 | 0.3310 | 0.0000 | 0.9900 | 0.0100 | | 1.480 | |
| 105.41 | 0.1507 | 0.5342 | 0.3151 | 0.1892 | 0.8044 | 0.0064 | 1.255 | 1.506 | 0.834 |
| 104.58 | 0.2895 | 0.4089 | 0.3017 | 0.3692 | 0.6173 | 0.0135 | 1.275 | 1.510 | 0.845 |
| 105.10 | 0.4179 | 0.3090 | 0.2731 | 0.5086 | 0.4872 | 0.0042 | 1.217 | 1.577 | 0.772 |
| 104.55 | 0.5400 | 0.2040 | 0.2560 | 0.6655 | 0.3303 | 0.0041 | 1.232 | 1.619 | 0.761 |
| 105.08 | 0.6563 | 0.0989 | 0.2448 | 0.8268 | 0.1680 | 0.0053 | 1.260 | 1.699 | 0.742 |
| 105.20 | 0.7433 | 0.0000 | 0.2567 | 0.9958 | 0.0000 | 0.0042 | 1.340 | | |

TABLE 1-continued

| | liquid phase composition | | | vapor phase composition | | | | | alpha(MEG/ |
|---|---|---|---|---|---|---|---|---|---|
| T/° C. | x(MEG) | x(1,2-BDO) | x(glycerol) | y(MEG) | y(1,2-BDO) | y(glycerol) | K(MEG) | K(1,2-BDO) | 1,2-BDO) |
| | 50 wt. % glycerol in feed | | | | | | | | |
| 109.32 | 0.0000 | 0.5200 | 0.4800 | 0.0000 | 0.9811 | 0.0189 | | 1.887 | |
| 109.42 | 0.1743 | 0.3657 | 0.4600 | 0.2626 | 0.7234 | 0.0140 | 1.507 | 1.978 | 0.762 |
| 108.69 | 0.3287 | 0.2292 | 0.4421 | 0.4811 | 0.5101 | 0.0089 | 1.464 | 2.226 | 0.658 |
| 109.14 | 0.4611 | 0.1209 | 0.4180 | 0.7082 | 0.2815 | 0.0102 | 1.536 | 2.328 | 0.660 |
| 109.88 | 0.5953 | 0.0000 | 0.4047 | 0.9901 | 0.0000 | 0.0099 | 1.663 | | |

That which is claimed is:

1. A process for the separation of monoethylene glycol (MEG) and 1,2-butanediol (1,2-BDO) from a first mixture comprising MEG and 1,2-BDO, said process comprising the steps of:
   (i) providing said first mixture comprising MEG and 1,2-BDO as a feed to a distillation column;
   (ii) providing a feed comprising glycerol to the distillation column above the first mixture;
   (iii) operating the distillation column at a temperature in the range of from 50 to 250° C. and a pressure in the range of from 0.1 to 400 kPa;
   (iv) removing a stream comprising MEG and glycerol as a bottoms stream from the distillation column; and
   (v) removing a stream comprising 1,2-BDO above the point at which the feed comprising glycerol is provided to the distillation column.

2. The process according to claim 1, wherein the stream comprising MEG and glycerol is subjected to a further distillation step in which MEG is distilled off to provide an MEG stream and a glycerol stream.

3. The process according to claim 2, wherein at least a portion of the glycerol stream is then recycled to the distillation column as the feed comprising glycerol.

4. The process according to claim 1, wherein the first mixture comprising MEG and 1,2-BDO is derived from the reaction product stream from a process for the hydrogenolysis of a saccharide-containing feedstock.

5. The process according to claim 1, wherein the mixture comprising MEG and 1,2-BDO has a weight ratio of MEG:1,2-BDO of at least 5:1.

6. The process according to claim 1, wherein the feed comprising glycerol is provided at the top of the distillation column.

7. The process according to claim 1, wherein the glycerol is added in an amount such that the weight ratio of the feed comprising glycerol to the first mixture comprising MEG and 1,2-BDO is at least 1:20 and at most 10:1 based on the overall weight of the feed/mixture.

8. The process according to claim 1, wherein the stream comprising MEG and glycerol comprises at least 99.6 wt % MEG.

9. The process according to claim 1, wherein monopropylene glycol (MPG) is present in the first mixture comprising MEG and 1,2-BDO and a stream comprising MPG is removed as the overheads stream from the distillation column and a side stream comprising 1,2-BDO is removed at some point below the overheads stream and above the glycerol feed.

* * * * *